United States Patent [19]

Kordes

[11] Patent Number: Plant 5,411

[45] Date of Patent: Mar. 5, 1985

[54] ROSE PLANT KORAMPA OF THE FLORIBUNDA CLASS

[75] Inventor: Reimer Kordes, Sparrieshoop, Fed. Rep. of Germany

[73] Assignee: Jackson & Perkins Company, Medford, Oreg.

[21] Appl. No.: 485,278

[22] Filed: Apr. 15, 1983

[51] Int. Cl.[3] ..... A01H 5/00

[52] U.S. Cl. ..... Plt./24

[58] Field of Search ..... Plt./22, 24

*Primary Examiner*—Robert E. Bagwill

*Attorney, Agent, or Firm*—Klarquist, Sparkman, Campbell, Leigh & Whinston

[57] ABSTRACT

A floribunda rose variety having a pale orange bud and flower, stiff and heavy textured petals, large foliage, resistance to rose powdery mildew, few thorns, straight stems, and slight fragrance.

1 Drawing Figure

This present invention relates to a new and distinct variety of rose plant of the floribunda class which was originated by me by crossing the variety ANABELL with an unnamed variety.

The primary objective of this breeding was to produce a new rose variety suitable for use as a cut flower in a pastel to ivory shade. This objective was substantially achieved along with other desirable improvements as evidenced by the following unique combination of characteristics which are outstanding in the new variety and which distinguish it from its parents, as well as from all other varieties of which I am aware:

1. Bud and flower color of a pale orange tint, equivalent to R.H.S. group 20, C and B.
2. Stiff, heavy textured petals, opening slowly to a well imbricated open flower.
3. Large foliage, resistant to rose powdery mildew.
4. Few, straight thorns.
5. Straight, rigid stems.
6. Slight fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Anabell.

*Pollen parent.*—Unnamed variety.

Classification:

*Botanical.*—Rosa hybrid.

*Commercial.*—Floribunda.

FLOWER

Observations made from specimens grown in a greenhouse at Irvine, Calif. in November.

Blooming habit: Continuous.

Bud:

*Size.*—1" When petals start to unfurl.

*Form.*—Long, blunt top.

*Color.*—When sepals first divide, Near Orange 27A. When half blown; upper side of petals Orange 27A; lower side of petals Orange 27A.

*Sepals.*—Color: Outer surface Green 138B. Three appendaged sepals lightly appendaged. Two unappendaged sepals glandular edged.

*Receptacle.*—Color: Green 138B. Shape: Narrow funnel. Size: Small, slender. Surface: Smooth.

*Peduncle.*—Length: Short. Surface: Prickly. Color: Light green. Strength: Stiff, erect.

Bloom:

*Size.*—Medium. Average open size: 3".

*Borne.*—Singly and several together.

*Stems.*—Medium, strong.

*Form.*—When first open, high center. Permanence: Outer petal edges slightly curled.

Petalage.—Number of petals under normal conditions: 20–25.

*Color.*—Center of flower: Upper side of petals Yellow-Orange 20C; distal portions of petals Yellow-Orange 20D; reverse side of petals Yellow-Orange 20C; base of petals Yellow-Orange 20B. General tonality from a distance Yellow-Orange 20C.

*Variegations.*—None.

*Discoloration.*—General tonality at end of first day: Yellow-Orange 20C. Third day: Yellow-Orange 20D.

*Fragrance.*—Slight.

Petals:

*Texture.*—Thick.

*Shape.*—Nearly round.

*Form.*—Edges slightly quilled.

*Arrangement.*—Imbricated. Petaloids in center, few.

*Persistence.*—Drop off cleanly.

*Lastingness.*—On the plant, long. As cut flower, long.

Reproductive parts:

*Anthers.*—Medium, many. Color: Yellow. Arrangement: Regular around styles.

*Filaments.*—Color: White.

*Pollen .*—Lemon yellow.

*Styles.*—Yellow.

*Stigmas.*—Color: White, red on distal half.

PLANT

Form: Bush.
Growth: Very vigorous, upright.
Foliage: Number of leaflets on normal mid-stem leaves: 5.
*Size.*—Large.
*Quantity.*—Normal.
*Color.*—New foliage: Grayed Purple 183C. Old foliage: Yellow-Green 146A.
Leaflets:
*Shape.*—Oval pointed.
*Texture.*—Upper side: Leathery.
*Edge.*—Serrated.
*Serration.*—Single, small.
*Petiole.*—Rachis: Color: Green. Underside: Prickles.
*Stipules.*—Long, serrated.
*Disease resistance.*—Resistant to mildew under normal growing conditions at irvine, Calif.

Wood:
*New wood.*—Color: Reddish. Bark: Smooth.
*Old wood.*—Color: Green. Bark: Smooth.
Prickles:
*Quantity.*—On main stalks from base, few. On laterals from stalk, few.
*Form.*—Long, straight.
*Color when young.*—Red.
*Position.*—Irregular.
Small Prickles:
*Quantity.*—On main stalks, none. On laterals, none.

I claim:

1. A new and distinct variety of rose plant of the floribunda class, substantially as herein shown and described, characterized particularly as to novelty by the unique combination of its pale orange-ivory flower color, heavy textured petals, large foliage, resistance to rose powdery mildew, few thorns, straight stems and slight fragrance.

* * * * *

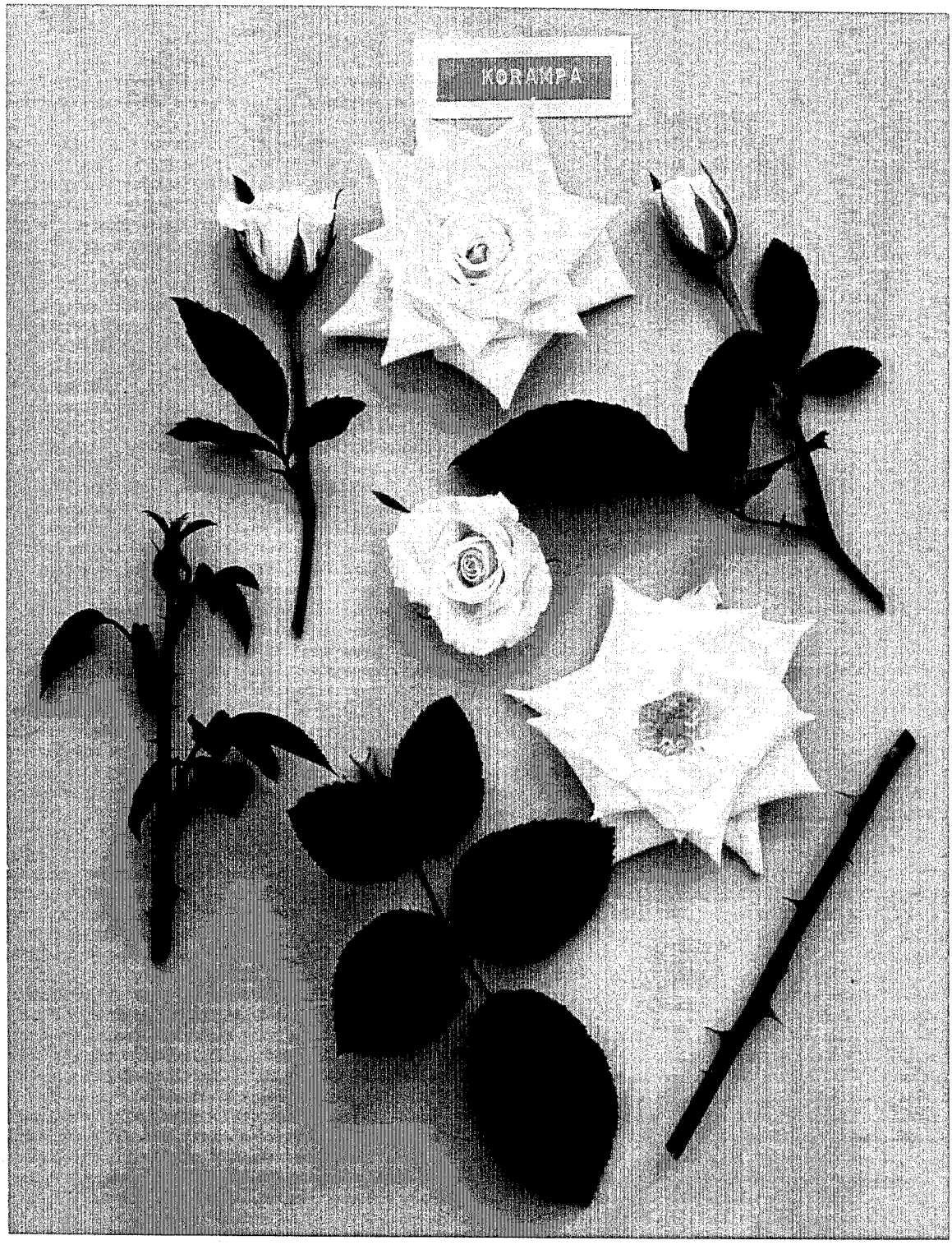
KORAMPA